(12) United States Patent
Gerdes et al.

(10) Patent No.: US 10,568,983 B2
(45) Date of Patent: Feb. 25, 2020

(54) WOUND DRESSING MATERIAL AND METHOD FOR ITS PRODUCTION

(71) Applicant: Sefar AG, Heiden (CH)

(72) Inventors: Gerd Gerdes, Abtwil (CH); Jeremie Weber, Klaus (AT); Alexander Hausser, Kreuzlingen (CH)

(73) Assignee: Sefar AG, Heiden (CH)

( * ) Notice: Subject to any disclaimer, the term of this patent is extended or adjusted under 35 U.S.C. 154(b) by 408 days.

(21) Appl. No.: 15/522,711

(22) PCT Filed: Jul. 9, 2015

(86) PCT No.: PCT/EP2015/065668
§ 371 (c)(1),
(2) Date: Apr. 27, 2017

(87) PCT Pub. No.: WO2016/062417
PCT Pub. Date: Apr. 28, 2016

(65) Prior Publication Data
US 2018/0147315 A1    May 31, 2018

(30) Foreign Application Priority Data

Oct. 24, 2014   (EP) .................... 14190214

(51) Int. Cl.
| | | |
|---|---|---|
| *A61L 15/26* | (2006.01) | |
| *A61L 15/42* | (2006.01) | |
| *A61F 13/02* | (2006.01) | |
| *A61L 15/44* | (2006.01) | |
| *A61L 15/58* | (2006.01) | |

(52) U.S. Cl.
CPC .......... *A61L 15/26* (2013.01); *A61F 13/0206* (2013.01); *A61F 13/0226* (2013.01); *A61L 15/425* (2013.01); *A61L 15/44* (2013.01); *A61L 15/58* (2013.01)

(58) Field of Classification Search
CPC .......... A61L 15/26; A61L 15/44; A61L 15/58; A61L 15/425; A61L 15/22; A61F 13/0206; A61F 13/0226; A61F 13/023; A61F 13/00012; A61F 13/53; A61F 13/0273; A61F 13/00008; A61K 31/716
See application file for complete search history.

(56) References Cited

U.S. PATENT DOCUMENTS

| | | | | |
|---|---|---|---|---|
| 4,984,570 A * | 1/1991 | Langen | ............ | A61F 13/00008 602/44 |
| 6,140,550 A * | 10/2000 | Beihoffer | ............ | A61F 13/53 604/365 |
| 2002/0052570 A1* | 5/2002 | Naimer | ............ | A61F 13/0273 602/53 |
| 2004/0005364 A1* | 1/2004 | Klein | ............ | A61K 31/716 424/618 |
| 2009/0048571 A1* | 2/2009 | Catalan | ............ | A61L 15/22 604/367 |
| 2013/0150764 A1* | 6/2013 | Patel | ............ | A61F 13/00012 602/44 |

OTHER PUBLICATIONS

International Search Report and Written Opinion dated Oct. 9, 2015 for PCT/EP2015/065668 filed Jul. 9, 2015.
English Translation of the International Preliminary Report on Patentability dated Feb. 24, 2017 for PCT/EP2015/065668 filed Jul. 9, 2015. pp. 1-5.

* cited by examiner

*Primary Examiner* — Tarla R Patel
(74) *Attorney, Agent, or Firm* — Dinsmore & Shohl LLP

(57) ABSTRACT

The invention relates to a wound dressing material with a biocompatible monofilament fabric which forms a contact face on a wound and is designed as a carrier layer on which a cover element is applied and is firmly connected at least in parts to the carrier layer. The invention further relates to a method for producing such a wound dressing material, in which method a biocompatible monofilament fabric is formed as a first web material, a cover element is formed as a second web material, and the first web material and the second web material are brought together, wherein the biocompatible monofilament fabric and the cover element are firmly connected to each other, in particular welded, and the wound dressing material is produced as a band.

12 Claims, No Drawings

WOUND DRESSING MATERIAL AND METHOD FOR ITS PRODUCTION

The invention relates to a wound dressing material for placing onto a wound, in particular that of a human being, in accordance with the preamble of claim 1. The invention further relates to a method for producing such a wound dressing material in accordance with claim 12.

Wound materials of such type have been known as strip-shaped dressing materials or plasters for a long time. Normally, dressing materials consist of cotton fabric or another fiber material that has a certain absorptive capacity. In many cases this is desirable as the wound dressing material can thus receive and store an ointment or liquid to support the healing of the wound or receive wound secretions in order to keep the wound dry.

However, in the case of absorbent fiber materials there is the problem that these are susceptible to the attraction of germs. Therefore such dressing materials have to be changed relatively often for a good wound healing process.

However, a frequent change of the dressing material can even have a negative effect on wound healing, especially if tissue material adheres to the wound dressing and the wound is torn open during change.

Furthermore, it is known that a monofilament fabric is also provided as a wound dressing material. However, a fabric of such type shows a poor absorptive capacity for liquids, as is desired for a wound dressing.

From the generic U.S. Pat. No. 4,984,570 A a wound dressing material can be taken, in which a contact side is produced of synthetic threads together with natural threads by knitting a mesh structure in order to form a receiving area for wound secretions. By folding the textile material knitted in one piece a layered structure is brought about.

US 2002/0052570 A1 teaches an elastic, self-adhering bandage strip with a pad for absorbing wound secretions. On a contact side of the pad that makes contact with the wound a non-adhering contact layer is provided.

The invention is based on the object to provide a wound dressing material which is particularly beneficial to good wound healing. Furthermore, it is the object of the invention to provide a method for producing such a wound dressing material.

The object is achieved on the one hand by a wound dressing material having the features of claim 1 and on the other hand by a method having the features of claim 12. Preferred embodiments are stated in the dependent claims.

According to the invention a wound dressing material with a biocompatible monofilament fabric is provided, which forms a contact side onto a wound and is designed as a carrier layer, onto which a cover element is applied that is firmly connected at least in some areas to the carrier layer.

One aspect of the invention resides in a multi-layer structure of the wound dressing material, in which a contact side onto the wound is formed by a biocompatible monofilament fabric. The monofilament fabric is formed of monofilament threads, i.e. plastic wires. These monofilament threads are formed with a smooth, stable surface so that in contrast to multifilament threads no fiber material from the upper side of the threads can penetrate into the wound. Moreover, through a smooth surface less adhesion of tissue material of the wound to the contact side of the wound dressing material is achieved. This counteracts the risk of the wound being torn open when the wound dressing material is removed from the wound. This is soothing for a patient and promotes wound healing.

According to a further aspect of the invention the monofilament fabric is of biocompatible design. The choice of the raw materials and the processing into the monofilament fabric are devised such that the monofilament fabric is non-irritating, in particular non-cytotoxic, pyrogen-free and hypoallergenic. Fabrics, as they are usually employed in the industry, are generally not biocompatible. However, biocompatible fabrics are known from the field of blood filtration. Biocompatibility of the fabric can be assumed in particular if the requirements according to ISO 10993 or of the "Class VI-test" of the USP (United States Pharmacopeia) are met.

Through biocompatibility it is ensured that on the one hand an irritation of the injured tissue material by the wound dressing material is largely prevented and on the other hand the risk of the wound being harmed, in particular being torn open during removal of the wound dressing material is counteracted.

Moreover, according to a further aspect of the invention the biocompatible monofilament fabric is of such stable design that it serves as a carrier layer, on which at least one cover element is firmly fixed. This cover element can itself have a single layer or several layers. According to the purpose of application of the wound dressing material the cover element can be designed in a desired way, e.g. to receive wound secretions or to apply means promoting wound healing such as an ointment or a liquid.

According to the invention different elements and materials can be provided to form the cover element as these are arranged on the upper side facing away from the contact side of the monofilament fabric and therefore do not make direct contact with the tissue material in the wound area. The cover element itself can have a multi-layer structure.

A preferred embodiment of the invention resides in the fact that the monofilament fabric is formed as a single-weave fabric with an open-mesh structure having a pore size ranging from 5 µm to 500 µm, preferably from 20 µm to 300 µm, and that the pores constitute a proportion of 15% to 70% of the surface of the monofilament fabric. Thus, according to this embodiment the monofilament fabric according to the invention is particularly fine-pored, allowing on the one hand air and liquid to pass through the pores while on the other hand a fusing or clutching of the monofilament fabric by tissue material is hardly feasible. In this way, a protective and yet permeable wound dressing is created which still ensures a clear demarcation and therefore easy removability from the wound. Good permeability for air and liquid is given in particular by the fact that the pores constitute a proportion of 15% to 70%, preferably 40% to 70% of the surface of the monofilament fabric. In this way, a high permeability is attained.

The monofilament fabric is designed as a single-weave fabric having a substantially two-dimensional fabric construction with a single warp thread system and a single weft thread system. Moreover, by making use of a transparent thread material for the monofilament threads in combination with the large pore surface a very high transparency is achieved. Despite a relatively thin fabric thickness a sufficient stability of the carrier layer formed by the monofilament fabric, along with a good fabric openness, a taffeta 1:1 can be achieved by a plain weave. Another stable construction can be achieved by a twill weave in any pattern repeats, preferably in a 1:2, 1:3, 2:2 and 3:3 weave regarding warp thread/weft thread arrangement. Another stable weave is possible by a satin weave in any pattern repeats, by particular preference in a 1:7 satin weave regarding warp thread/ weft thread arrangement. A further possible stable weave for the monofilament fabric is a plain reverse Dutch weave.

According to a further development of the invention it is preferred that the monofilament threads of the monofilament fabric are formed of PA, PET, PP, PVDF and/or PTFE and have a diameter size ranging between 20 µm and 500 µm, preferably between 30 µm and 150 µm. The monofilament threads are produced of a particularly pure basic material so that these comply with food legislation. Pyrogen-free and non-cytotoxic fabrics can be produced. A particularly preferred material is polyamide PA 6.6 in a purified and biocompatible state. Depending on the application the thread diameters can vary but preferably they are kept as small as possible. In particular, the monofilament threads are designed with a longitudinal rib structure, in which the longitudinal ribs protrude radially from a core diameter of the monofilament thread by a maximum of 0.5 µm to 5 µm. This very fine rib design furthermore ensures a relatively smooth surface of the monofilament threads while providing at the same time adequate stability at the points of intersection of the monofilament threads in the fabric and therefore a stable shape of the pores. In addition, the monofilament fabric can be calendered.

Another preferred embodiment of the invention resides in the fact that the contact side is provided at least in some areas with an adhesive layer. Usually, the adhesive layer is an application of adhesive that is suitable for being applied to the skin. The adhesive layer can be applied directly onto the contact side of the monofilament fabric.

Preferably, this embodiment of the invention is developed further in that the adhesive layer is applied in a strip-shaped manner along a marginal area of the contact side of the monofilament fabric and in that the upper side of the marginal area of the monofilament fabric which faces away from the contact side is kept free from the cover element.

Hence, in this embodiment the cover element does not extend over the entire surface of the monofilament fabric but only in a center area while a strip-shaped marginal area is kept free. The marginal area can only extend along a partial area of the external circumference or be designed along the entire external circumference and therefore be closed in a ring-shaped manner. The strip-shaped adhesive layer allows the wound dressing material to be fixed in a spaced manner from the wound. By keeping the upper side of the marginal area free a sufficient access of air is rendered possible and an irritation of the skin caused by the adhesive layer is counteracted.

The marginal area of the wound dressing material is trimmed, in particular through thermal trimming (heat cutting), in which the cut edges are welded and rounded off. The adhesive layer can also be applied to a contact element which is in turn applied along the marginal area of the monofilament fabric. This contact element can be folded around the marginal edge of the monfilament fabric and can trim this in addition so as to thereby increase the wearing comfort further.

According to a further development of the invention it is advantageous for the cover element to have a fabric, a non-woven textile, a film, a membrane and/or a foam. In particular, the cover element itself can have a layer-wise or multi-ply structure, in which the individual layers or plies are themselves formed of identical or different materials. When using a fabric, a multifilament fabric with an increased absorptive capacity can also in particular be applied in addition to a further monofilament fabric. For this purpose, non-woven textiles, such as a knitted fabric, a fleece, felt or the like or even cotton wool can also be employed. These materials are also well-suited to receive care substances or medically effective substances. To protect against the entry of liquids, gases or other physical influences from the outside provision can be made for a film, a membrane and/or a foam. By preference, the membrane can be semi-permeable, allowing an exchange of gas while preventing the entry of liquid from the outside into the wound or, vice versa, the leakage of liquid from the wound into an external area.

According to the invention provision is made for the cover element to be spot-welded to the monofilament fabric. This can be implemented through thermal welding or preferably through ultrasonic welding. The welding process can also be effected during heat cutting or laser cutting in the marginal area. Along the marginal area the cover element can be welded in a linear manner to the monofilament fabric so that the cover element is in particular closed in an all-embracing or annular manner on its external side.

Another advantageous embodiment of the invention resides in the fact that the cover element has an external cover layer which is connected to the monofilament fabric by forming at least one receiving area. The at least one receiving area can be a hollow space, in which a further element is provided to receive liquid or a substance. The external cover layer can be a film or a membrane in particular which forms a liquid-tight closure towards the outside. In this way it can be ensured in particular that items of clothing worn on the wound dressing material do not become soiled by substances from the wound dressing material or by wound secretions.

To reduce tissue irritation provision is made according to a further embodiment variant of the invention that the thickness of the upper side formed by the cover element amounts to 60% to 98% of the overall thickness of the wound dressing material. The biocompatible monofilament fabric is very fine and has a thickness of 40 µm to 1 mm, preferably ranging between 70 µm and 300 µm. Depending on the application the cover element which forms the upper side of the wound dressing material can range from 60 µm up to a few milimeters.

To promote wound healing provision is made according to a further embodiment pursuant to the invention that the cover element has a care substance or medically effective substance. The cover element can be a reservoir with a liquid or gel filling or be designed to receive powders or solids.

Basically, provision is made for the monofilament threads to be produced of a plastic material high in purity and in such a manner that these have a surface as smooth as possible by themselves. An advantageous embodiment of the invention resides in the fact that the monofilament fabric or the monofilament threads that form the monofilament fabric are provided with a coating. With this coating the surface can be treated and influenced in a desired way. In particular, a hydrophilic or hydrophobic coating is possible. Moreover, the coarseness and adhering property of the surface can be reduced further. In addition to such a surface coating with suitable materials it is also possible to set a different surface modification, especially a smoothing of the thread surfaces or the surface of the finished monofilament fabric.

Another advantageous embodiment of the invention can be seen in the fact that the monofilament fabric is woven with a uniform defined pore size, wherein the pore sizes do not differ from each other by more than 10%, preferably by less than 5%. Thus, a monofilament fabric is created that has a highly uniform pore size across the entire surface. Depending on the purpose of application a pore size as appropriate as possible can be provided which allows on the one hand the passage of air or liquid in the desired way while on the other hand the risk of ingrowth or clutching of tissue material is counteracted to a large degree.

According to the invention provision is made for a method for producing a wound dressing material as described beforehand in particular, in which a biocompatible monofilament fabric is formed as a first web material, a cover element is formed as a second web material, the first web material and the second web material are brought together, wherein the biocompatible monofilament fabric and the cover element are firmly connected, in particular welded to each other, and the wound dressing material is produced as a tape. The tape thus produced can be wound up to a roll or cut and tailored in the desired way.

The method according to the invention permits an efficient production of the wound dressing material in a continuous process. The basic materials are preferably supplied as tape-shaped webs from rolls. The cover element can be a prefabricated web material that consists of several layers. It is also possible that the cover element is formed of several web materials that are supplied simultaneously and connected to the monofilament fabric.

The invention claimed is:

1. Wound dressing material having a cover element for receiving wound secretions or for applying means promoting wound healing and a contact side for placing onto the wound,
wherein
the contact side is formed by a biocompatible monofilament fabric consisting of monofilament threads of PET with a smooth stable surface,
the PET-monofilament threads have a diameter size ranging between 20 μm and 500 μm, and
wherein the monofilament fabric is designed as a carrier layer with an upper side which faces away from the wound and onto which the cover element is applied and firmly connected in some areas to the carrier layer through spot welding wherein the monofilament fabric is formed as a single-weave fabric with an open-mesh structure having a pore size ranging from 5 μm to 500 μm, preferably from 20 μm to 300 μm, and wherein the pores constitute a proportion of 15% to 60% of the surface of the monofilament fabric.

2. Wound dressing material according to claim 1, wherein
the monofilament threads of the monofilament fabric have a diameter size ranging between 50 μm and 150 μm.

3. Wound dressing material according to claim 1, wherein
the contact side is provided at least in some areas with an adhesive layer.

4. Wound dressing material according to claim 3, wherein
the adhesive layer is applied in a strip-shaped manner along a marginal area of the contact side of the monofilament fabric and
wherein that the upper side of the marginal area of the monofilament fabric which faces away from the contact side is kept free from the cover element.

5. Wound dressing material according to claim 1, wherein
the cover element has a fabric, a non-woven textile, a film, a membrane and/or a foam.

6. Wound dressing material according to claim 1, wherein
the cover element is spot-welded to the monofilament fabric through ultrasonic welding.

7. Wound dressing material according to claim 1, wherein
the cover element has an external cover layer which is connected to the monofilament fabric by forming at least one receiving area.

8. Wound dressing material according to claim 1, wherein
the thickness of the upper side formed by the cover element amounts to 60% to 98% of the overall thickness of the wound dressing material.

9. Wound dressing material according to claim 1, wherein
the cover element has a care substance or medically effective substance.

10. Wound dressing material according to claim 1, wherein
the monofilament fabric or the monofilament threads that form the monofilament fabric are provided with a coating.

11. Wound dressing material according to claim 1, wherein
the monofilament fabric is woven with a uniform defined pore size, wherein the pore sizes do not differ from each other by more than 10%.

12. Method for producing a wound dressing material according to claim 1, in which
a biocompatible monofilament fabric consisting of monofilament threads of PET with a smooth stable surface is formed as a first web material,
a cover element is formed as a second web material, wherein the PET-monofilament threads have a diameter size ranging between 20 μm and 500 μm,
the first web material and the second web material are brought together, wherein the biocompatible monofilament fabric is provided as a carrier layer with an upper side which faces away from the wound and onto which the cover element is applied and firmly connected thereto through spot welding, and
the wound dressing material is produced as a tape.

* * * * *